(12) United States Patent
Miyashita

(10) Patent No.: US 10,942,115 B2
(45) Date of Patent: Mar. 9, 2021

(54) DARK-ENVIRONMENT SIMULTANEOUS CULTURING OBSERVING APPARATUS

(71) Applicant: Mitsuyoshi Miyashita, Saitama (JP)

(72) Inventor: Mitsuyoshi Miyashita, Saitama (JP)

(*) Notice: Subject to any disclaimer, the term of this patent is extended or adjusted under 35 U.S.C. 154(b) by 109 days.

(21) Appl. No.: 15/570,808

(22) PCT Filed: May 1, 2015

(86) PCT No.: PCT/JP2015/063129
§ 371 (c)(1),
(2) Date: Oct. 31, 2017

(87) PCT Pub. No.: WO2016/178277
PCT Pub. Date: Nov. 10, 2016

(65) Prior Publication Data
US 2018/0156722 A1   Jun. 7, 2018

(51) Int. Cl.
*G01N 21/35* (2014.01)
*C12M 1/00* (2006.01)
(Continued)

(52) U.S. Cl.
CPC ............ *G01N 21/35* (2013.01); *C12M 1/00* (2013.01); *C12M 1/002* (2013.01); *C12M 1/34* (2013.01);
(Continued)

(58) Field of Classification Search
CPC .......... C12M 1/00; C12M 1/002; C12M 1/34; C12M 41/36; C12Q 1/02; C12Q 1/06;
(Continued)

(56) References Cited

U.S. PATENT DOCUMENTS

| | | | | |
|---|---|---|---|---|
| 5,360,722 A | * | 11/1994 | Inoue | G01N 1/2273 435/286.6 |
| 6,381,353 B1 | * | 4/2002 | Weiss | C12M 41/36 382/133 |
| 2009/0086314 A1 | * | 4/2009 | Namba | G02B 21/361 359/383 |

(Continued)

FOREIGN PATENT DOCUMENTS

| | | |
|---|---|---|
| JP | S60-184398 A | 9/1985 |
| JP | H01-222799 A | 9/1989 |

(Continued)

OTHER PUBLICATIONS

Mossoba, M. M. et al.: "Application of a Novel Hydrophilic Infrared-Transparent Membrane to the Differentiation between Microcolonies of *Enterobacter sakazakii* and *Klebsiella pneumoniae*", Journal of Food Protection, vol. 70, No. 5, 2007, pp. 1241-1245.

*Primary Examiner* — Gautam Prakash
*Assistant Examiner* — Lydia Edwards
(74) *Attorney, Agent, or Firm* — Harness, Dickey & Pierce, P.L.C.

(57) ABSTRACT

A dark-environment simultaneous culturing-observing apparatus includes: an observation-subject holding unit for holding an observation subject; a dark-environment culturing chamber for culturing, in a dark environment, bacteria in the observation subject held by the observation-subject holding unit; an infrared light source for irradiating, with infrared light, the observation subject held by the observation-subject holding unit kept in the dark-environment culturing chamber; and an infrared light camera for photographing the observation subject irradiated with infrared light from the infrared light source.

15 Claims, 12 Drawing Sheets

(51) Int. Cl.
*C12M 1/34* (2006.01)
*C12Q 1/00* (2006.01)
*G01N 15/00* (2006.01)
*C12Q 1/02* (2006.01)
*C12Q 1/06* (2006.01)
*G01N 15/02* (2006.01)
*G02B 21/36* (2006.01)

(52) U.S. Cl.
CPC ............... *C12M 41/36* (2013.01); *C12Q 1/02* (2013.01); *C12Q 1/06* (2013.01); *G01N 15/0205* (2013.01); *G02B 21/36* (2013.01); *G01N 2015/0065* (2013.01); *G01N 2015/03* (2013.01)

(58) Field of Classification Search
CPC ....... G01N 15/0205; G01N 2015/0065; G01N 2015/03; G01N 21/35; G02B 21/36
See application file for complete search history.

(56) References Cited

U.S. PATENT DOCUMENTS

2012/0275681 A1* 11/2012 Honda ................... C12M 33/00
382/133

FOREIGN PATENT DOCUMENTS

| JP | H04-218393 A | 8/1992 |
| JP | 2002-085054 A | 3/2002 |
| JP | 2003-038163 A | 2/2003 |
| JP | 2004-012398 A | 1/2004 |
| JP | 2005-055180 A | 3/2005 |
| JP | 2006-014825 A | 1/2006 |
| JP | 2006-330359 A | 12/2006 |
| JP | 2010-008492 A | 1/2010 |
| JP | 2012-075409 A | 4/2012 |
| JP | 2012-135240 A | 7/2012 |
| JP | 2014-044070 A | 3/2014 |
| JP | 2014-528253 A | 10/2014 |

* cited by examiner

DARK-ENVIRONMENT SIMULTANEOUS CULTURING OBSERVING APPARATUS

CROSS-REFERENCE TO RELATED APPLICATIONS

This application is a U.S. National Phase Application of International Application No. PCT/JP2015/063129, filed on May 1, 2015 and published in Japanese as WO/2016/178277 on Nov. 10, 2016. The entire disclosure of the above application is incorporated herein by reference.

BACKGROUND

Technical Field

The present invention relates to a technology for performing colony counting in food sanitation inspection or the like.

Background Art

Business operators producing or selling food or the like are obliged to conduct measuring inspection of indicator bacteria or the like on the food to be handled. For example, viable bacteria counts represent the number of microorganisms living in 1 g of inspection subject of food, and used as an indication for evaluating microbial contamination of the food. With regard to measurement of the viable bacteria, an official method based on the Food Sanitation Act specifies counting of colony counts formed by growth of viable bacteria by pouring the inspection subject into an agar medium and culturing the resultant subject for 24 hours or 48 hours. Examples of such an inspection subject include soft drinks, ice cream, edible poultry eggs, drinking milk and dairy products.

The above-described business operators and the like voluntarily inspect the food in order to confirm safety of the food at earlier timing in combination with such inspection based on the official method. In a colony counting apparatus used in such voluntary inspection, a medium is photographed with a camera, and minute colonies at an undetectable degree from a photographed image with naked eyes are detected by executing an image processing program, an image recognition program or the like on a computer. Thus, colony counting can be quickly performed without needing a long-term culture period such as 24 hours or 48 hours. Specific examples of such a colony counting apparatus include a technology described in JP 2012-75409.

According to the technology described in JP 2012-75409, colony counting is performed by irradiating a medium with white light and identifying colonies from an image formed with light transmitted through the medium. More specifically, a difference is generated in a quantity of transmission of white light applied for irradiation between a portion in which the colonies are formed, and a portion in which no colonies are formed in the medium, and the difference appears as shade in a photographed image. Then, binarization processing or gray-scale processing is applied to the photographed image in which the shade appears, a dense portion is extracted as the colonies, and colony counting is performed. A speed is increased by applying image processing to the photographed image and performing colony counting in comparison with visual colony counting which has been performed so far.

Incidentally, according to colony counting which has been performed so far, as shown in FIG. 12, colony counting has been performed by removing a medium from a culturing apparatus every time when a predetermined elapsed time comes, such as after 12 hours, 18 hours and 24 hours from culture start, setting the medium in such a colony counting apparatus as described in JP 2012-75409, and photographing the medium. Such colony counting can be referred to as discrete observation.

On the other hand, as shown in the figure, growth of the colonies in the medium progresses continuously with elapse of time. A horizontal axis in the figure shows time elapsed from culture start, and a vertical axis shows contrast of the shade acquired from the photographed image of the medium. The contrast of the shade is caused by a difference in lightness between a dark portion and a light portion in the image. As mentioned above, predetermined contrast of the shade should be produced in order to identify and count the colonies. For example, in the figure, no contrast at a countable degree is produced in a stage of elapse of 18 hours.

Here, when colony counting is performed at an interval of 6 hours from culture start as in conventional colony counting, colony counting is first performed in a stage of elapse of 18 hours. However, colony counting can be practically performed around after elapse of 13 hours, which is earlier thereto. More specifically, observation is to be conducted after about 5 hours from the time at which colony counting can be performed at earliest, which can be referred to as having wasted time. Thus, according to such discrete observation which has been conducted so far, an interval is caused between a time to be countable and a time when observation is actually conducted, and the interval hinders colony counting at early timing.

To cope with the problem, a way of thinking of shortening an observation interval is also available. However, the discrete observation remains unchanged, and therefore the problem is not solved in a basic manner. Moreover, shortening of the observation interval means frequently putting the medium in and out from a culture apparatus to cause variations in culture conditions and therefore is undesirable for culture which is to be performed under constant conditions as much as possible. Accordingly, the problem of performing colony counting at early timing is far from being solved.

SUMMARY OF THE INVENTION

In order to solve the above-described problem, the present inventor has come to realize acquisition of an image by placing a medium in a culturing chamber for performing culture in a dark environment, and simultaneously irradiating a subject with infrared light having a larger difference in absorbance between the medium and colonies, and having properties of being harder to scatter than visible light in order to easily acquire the image having clear contrast of shade even in the culturing chamber in the dark environment. According to the present invention, colony counting can be performed at early timing by forming a configuration in such a manner that observation can be conducted while culturing the medium.

More specifically, the present invention provides a dark-environment simultaneous culturing-observing apparatus having an observation-subject holding unit for holding an observation subject, a dark-environment culturing chamber for culturing, in a dark environment, bacteria in the observation subject held in the observation-subject holding unit, an infrared light source for irradiating, with infrared light, the observation subject held in the observation-subject holding unit kept in the dark-environment culturing chamber, and an infrared light camera with which an image of the observation subject irradiated with the infrared light from the infrared light source is photographed.

Moreover, the present invention provides the dark-environment simultaneous culturing-observing apparatus, having the configuration, and further having a control unit for performing multiple photographing control for continuously photographing the observation subject with the infrared light camera over multiple times.

Moreover, the present invention provides the dark-environment simultaneous culturing-observing apparatus, having the configuration, in which, as the infrared light source, near-infrared light is irradiated. The present invention also provides the dark-environment simultaneous culturing-observing apparatus, having the configuration, in which the infrared light source is provided with a filter for blocking a predetermined wavelength band of near-infrared light. Moreover, the present invention provides the dark-environment simultaneous culturing-observing apparatus, having the configuration, in which the infrared light camera is provided with a filter for blocking a predetermined wavelength band of near-infrared light.

Moreover, the present invention further provides the dark-environment simultaneous culturing-observing apparatus, having the configuration, in which the infrared-light camera is arranged in being directed downward on a side of a ceiling in the dark-environment culturing chamber, the infrared light source is arranged in being directed upward on a side of a floor in the dark-environment culturing chamber, and the observation-subject holding unit is arranged between the infrared light camera and the infrared light source.

Moreover, the present invention provides the dark-environment simultaneous culturing-observing apparatus, having the configuration, in which bacteria being the observation subject are arranged in a membrane filter. Moreover, the present invention provides the dark-environment simultaneous culturing-observing apparatus, having the configuration, in which, as the observation subject, a depthwise distribution bacteria source medium formed by pouring a bacteria source into a medium.

The present invention provides a culturing-observing method using any one of the dark-environment simultaneous culturing-observing apparatuses, and the culturing-observing method using the dark-environment simultaneous culturing-observing apparatuses, having an observation subject placing step for placing an observation subject prepared by adding a bacteria source to a medium in order to culture bacteria in a dark environment in a dark environment culturing chamber, an infrared light irradiation step for irradiating the observation subject kept in the dark-environment culturing chamber with infrared light from the infrared light source, and a photographing step for photographing the observation subject by the infrared light camera in a state in which the observation subject is irradiated with infrared light from the infrared light source.

Moreover, the present invention provides the culturing-observing method, having the steps, in which the photographing step further has a control substep for performing multiple photographing control for continuously photographing the observation subject with the infrared light camera over multiple times. Moreover, the present invention provides the culturing-observing method, having the steps, in which the observation subject placing step has a depthwise distribution bacteria source medium production substep for producing a depthwise distribution bacteria source medium by pouring a bacteria source into a medium raw material.

Advantageous Effects of Invention

According to the present invention, colony counting can be performed at earlier timing by performing observation while performing culture.

DETAILED DESCRIPTION

Hereinafter, embodiments according to the present invention will be described with reference to drawings. In addition, the present invention is not limited by the embodiments at all, and may be practiced in various aspects within the scope without departing from the spirit.

Embodiment 1

Embodiment 1 Outline

A dark-environment simultaneous culturing-observing apparatus according to the present embodiment has features of having an infrared light source and an infrared light camera for photographing an image of an observation subject in a culture process in a dark-environment culturing chamber while bacteria contained in an inspection subject are cultured in the dark-environment culturing chamber.

The image formed by irradiating the subject with infrared light in a dark-environment chamber preferable for culture of bacteria can be photographed, and therefore observation for colony counting based on a photographed image thereof while culturing the bacteria can be conducted, and simultaneously the photographed image having resolution superior to resolution in the case of irradiating the subject with visible light can be acquired by photographing the image by irradiating the subject with infrared light, which contributes to enabling colony counting at early timing.

As described above, in infrared light, a difference in absorbance between a medium and colonies is larger in comparison with visible light. In particular, when the medium having low transparency is used, such as a medium obtained by pouring cow's milk thereinto, a blood medium and a chocolate medium is used, the absorbance of the medium is high comparably with the absorbance of the colonies when visible light is used, but when infrared light is used, the difference is caused in the absorbance between both. Accordingly, a case of irradiating the subject with infrared light has an advantage of easily acquiring contrast of shade caused by the medium and the colonies as the image in comparison with a case of irradiating the subject with visible light.

Moreover, infrared light has properties of being harder to scatter than visible light such as white light. Accordingly, in the image photographed by irradiating the subject with infrared light, a boundary between a portion in which the colonies exist and a portion in which no colonies exist becomes clearer. Accordingly, even when colonies so small as identifiable only as one lump in the image photographed by irradiating the subject with visible light, individual small colonies can be separately identified in the image photographed with infrared light. More specifically, in the case of irradiating the subject with infrared light, the image having resolution superior thereto can be photographed, and the colonies can be extracted with higher definition, and colony counting can be performed at early timing by such operation.

Embodiment 1 Configuration

Figure 1:
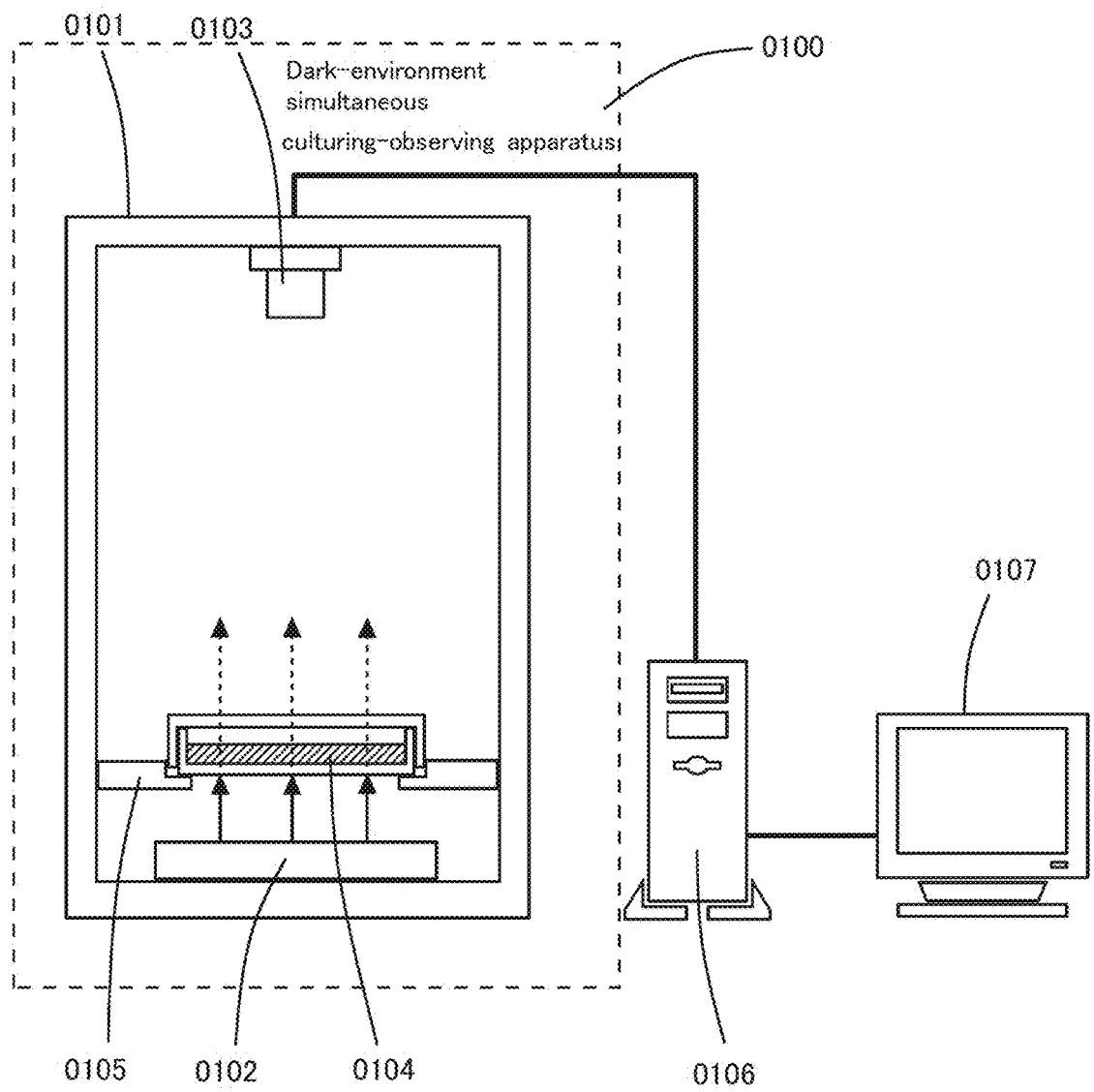
FIG. 1 is a schematic diagram showing each configuration of a dark-environment simultaneous culturing-observing apparatus in Embodiment 1.

FIG. 1 is a schematic diagram showing each configuration of the dark-environment simultaneous culturing-observing apparatus of the present embodiment. As shown in the figure, a "dark-environment simultaneous culturing-observing apparatus" (0100) has a "dark-environment culturing chamber" (0101), an "infrared light source" (0102) and an "infrared light camera" (0103). Then, an "observation-subject holding unit" (0105) for holding an "observation subject" (0104) is placed between the infrared light camera and the infrared light source. In the figure, a "computer" (0106) for identifying colonies from an image of the observation subject photographed by the infrared light camera and performing counting or the like, and a "display" (0107) for outputting a photographed image, the results of colony counting or the like are also shown. In addition, with regard to arrows in the figure, solid line arrows represent infrared light with which an observation subject is irradiated, and broken line arrows represent infrared light transmitted through the observation subject.

In the "observation-subject holding unit" (0105), the observation subject is held. The observation subject is a container such as a petri dish arranged by storing bacteria such as viable bacteria and a coliform group, fungi or the like serving as the inspection subject of sanitation inspection or the like, and a medium for providing the inspection subjects with a growth environment. Moreover, when a membrane filter or the like is used, such a material also serves as the observation subject. In the figure, a "petri dish" (0106) arranged by storing a medium on which a sample is poured serves as the observation subject. Various specific aspects for holding the observation subject are provided, and specific examples include a plate for placing the petri dish in a predetermined position, and a jig for clamping the petri dish from both sides. The observation-subject holding unit can be appropriately selected according to an aspect of the container serving as the observation subject, or culture, an aspect of photographing or the like.

The "dark-environment culturing chamber" (0101) is a chamber for culturing the bacteria in the observation subject in a dark environment. The chamber is not particularly limited as long as the chamber is suitable for culture, and upon being closed, an inside of the chamber is formed into the dark environment. For example, an incubator or the like can be used as the dark-environment culturing chamber. Moreover, creation of the dark environment also means prevention of being influenced by visible light upon photographing the observation subject by irradiating the subject with infrared light. Moreover, an environment in which a product such as food is stored is in the dark environment in many cases, and therefore the sanitation inspection on the assumption of the environment in which the product to be cultured in the dark environment is practically placed can be conducted.

Moreover, the medium for culturing bacteria and a culturing method can be appropriately selected according to the bacteria or a purpose of inspection. The culturing method has generally classified into a pour plate method and a spread plate method. The pour plate method is a method for culturing the medium prepared by pouring a bacteria source into the medium. Specifically, a sample is mixed with a heated and melted agar medium or the like, kept in a container such as a petri dish, and then solidified with temperature decrease, and the thus obtained medium is cultured. The thus prepared medium is referred to as a "depthwise distribution bacteria source medium" in the present description.

The spread plate method is a method in which the melted agar medium is kept in the container such as the petri dish and solidified, and then a sample is spread on a surface of the medium and inoculated. In the spread plate method, colonies are formed on the surface of the medium, and therefore a shape thereof or the like can be observed in detail. However, the sample can be inoculated only on the surface of the medium, and therefore an amount of the sample inoculated thereinto is small and a detection limit is reduced.

In contrast, in the pour plate method, the sample can be inoculated into the medium, and therefore the amount of the sample inoculated thereinto is large, and the detection limit is high. Accordingly, the method is advantageous for bacteria detection when bacteria counts in the sample are small as in measurement of viable bacteria counts or measurement of coliform group. However, the colonies are formed in the medium, and therefore the detection thereof can be referred to be more difficult than in the spread plate method.

Moreover, culture may also be performed using a membrane filter. The membrane filter is used for separating particulates or microorganisms of about 0.2 to several micrometers by filtration, and is a membrane of a porous body having integral and continuous pores. As a raw material thereof, cellulose, PVDF (polyvinylidene fluoride), PTFE (polytetrafluoroethylene), polyethylene, nylon or the like is used.

Culture by means of the membrane filter is applied to inspection of soft drinks or the like in food sanitation inspection, in which the soft drinks are filtered through the membrane filter, and the membrane filter after filtration is attached onto the surface of an agar medium solidified in the petri dish and fitted for the purpose, and cultured. The method is preferable when the amount of sample is presumed to be large and the bacteria counts are presumed to be small. The colonies formed on the membrane filter have been detected so far solely based on the image photographed with reflected light because visible light is hard to transmit through the membrane filter. However, the infrared light in the present embodiment transmits through the membrane filter, and therefore the colonies can be detected by detection based on the image photographed with transmitted light.

The medium and the culturing method are selected in such a manner that, for example, in inspection of the viable bacteria counts, the culture is performed in a standard agar medium by the pour plate method, in inspection of the coliform group, the culture is performed in a desoxycholate agar medium by the pour plate method, and in inspection of Staphylococcus aureus, the culture is performed in a yolk-added mannite salt agar medium onto which the sample is spread.

The "infrared light source" (0102) is provided for irradiating, with infrared light, the observation subject kept in the dark-environment culturing chamber. The infrared light source is a light source emitting infrared light being light having a wavelength generally in the range of 0.7 µm to 1,000 µm. From a viewpoint of a capability of photographing a whole region of the observation subject as the image, a form of the infrared light source is preferably a surface-emitting type having an area larger than an irradiation subject area of the observation subject. Specific examples thereof include an infrared light source formed by arranging a plurality of light-emitting elements such as LEDs emitting infrared light in a lattice form or in a concentric circle form and simultaneously provided with a diffusor. In addition, the irradiation subject area of the observation subject means, when the observation subject is a cylindrical petri dish, a bottom area of the petri dish, for example.

Figure 2:
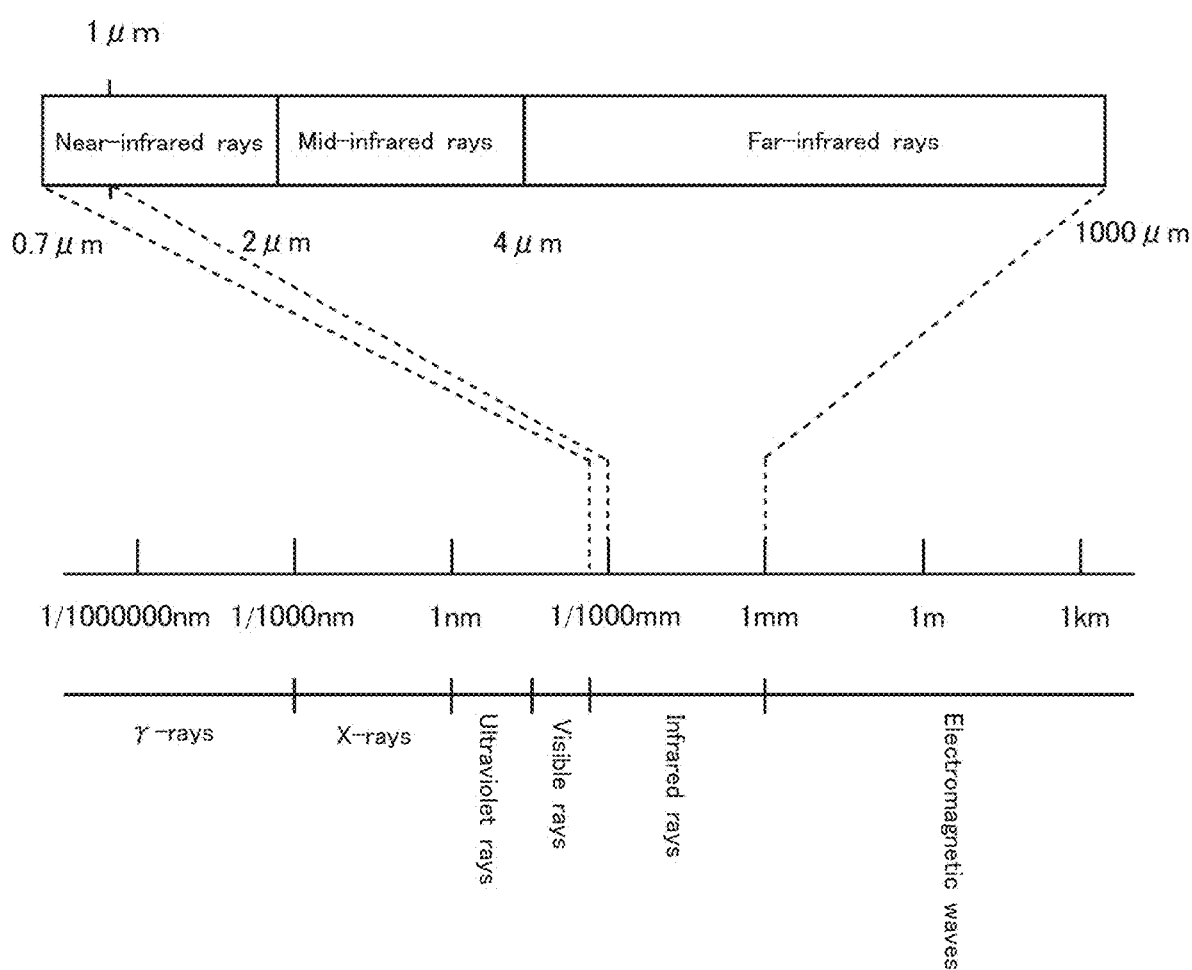
FIG. 2 is a schematic diagram showing a wavelength region of near-infrared light together with wavelength regions of other electromagnetic waves.

Moreover, the infrared light source is preferably a source emitting near-infrared light, and more specifically, a source emitting near-infrared light having a wavelength generally in the range of 0.7 µm to 1 µm. FIG. 2 is a schematic diagram showing the wavelength region of near-infrared light together with the wavelength regions of other electromagnetic waves. The reason therefor is that, in visible light having the wavelength (wavelength of 0.4 µm to wavelength of 0.7 µm) shorter than the wavelength of near-infrared light, the absorbance of the medium and the absorbance of the colonies become comparable to each other, and in the wavelength longer than 1 µm, absorbance by water becomes large, and light absorption of the medium containing a large amount of water increases, and a difference from light absorption of the colonies becomes small.

In order to render the wavelength region of the light emitted from the infrared light source to a desired wavelength region, the infrared light source having the light-emitting element designed to emit the infrared light in the desired range may be used, or when the region of the wavelength emitted from the light-emitting element is over the desired range, the infrared light source having a filter for blocking a wave band in a predetermined hyper-region by absorbing or reflecting the band may be used.

In addition, the infrared light irradiated from the infrared light source is emitted solely for photographing the subject, and therefore the subject need not be irradiated with the infrared light all the time. For example, the infrared light source may be configured to be controlled so as to irradiate the subject with infrared light on a timely basis, for example, when the irradiation is required for photographing the observation subject with the infrared light camera.

According to the "infrared light camera" (0103), the image of the observation subject irradiated with infrared light from the infrared light source is photographed. The "image" means an image obtained by receiving light transmitted through an object. Moreover, a digital infrared light camera is used for applying, to the photographed image or the like, image processing for identifying the colonies.

The infrared light camera may be a camera having an image pickup device (CCD, CMOS or the like) using a photodiode having responsivity in the wavelength region of infrared light. Various infrared light cameras having good responsivity in the desired wavelength region are commercially produced, and specific examples thereof include "ARTCAM-1000MI-WOM-OP (Artray Co., Ltd.)" and "C11440-52U (Hamamatsu Photonics K.K.)". In addition, the image is desired to be photographed with high definition, and therefore valid pixels of the infrared light camera are preferably 10 million or more.

Moreover, the infrared light camera may have a filter for blocking a predetermined wavelength band of infrared light. The infrared light camera may have the filter for blocking infrared light outside the wavelength the range of 0.7 µm to 1 µm being preferable for photographing the image of the observation subject, or a filter for blocking the wavelength in a visible light region, for example.

Here, an arrangement of the infrared light camera, the infrared light source and the observation subject each is described. First, the dark-environment simultaneous culturing-observing apparatus of the present embodiment is used for photographing the image of the observation subject irradiated with infrared light, and therefore the infrared light source and the infrared light camera are preferably arranged so that a direction of infrared light irradiation and a direction of photographing the image using the infrared light camera may face each other, and the observation subject is positioned between the infrared light source and the infrared light camera.

In FIG. 1, the infrared light camera is installed in being directed downward in a ceiling portion in the dark-environment culturing chamber, and the infrared light source is installed on a floor portion of the dark-environment chamber in being directed upward in irradiation light. Then, the petri dish serving as the observation subject is placed above the infrared light source. Such an arrangement is resulted from putting priority on a position of installing the infrared light camera. More specifically, the reason therefor is that the infrared light camera is preferably basically arranged in being directed downward. The reason therefor is that, if a lens of the infrared light camera is directed upward, dust or the lie existing in the dark-environment culturing chamber falls down on a surface of the lens and adhere thereonto in several cases, and the dust or the like adhered thereonto becomes a noise of the photographed image to hinder proper photographing.

Moreover, in FIG. 1, the petri dish is placed in a posture in which a lid of the petri dish is positioned above. The reason therefor is that, when the culture is performed by the spread plate method, the image having better contrast can be photographed in arranging the petri dish in such a manner the medium surface on which the sample spread thereon exists is directed toward the infrared light camera.

Figure 3:
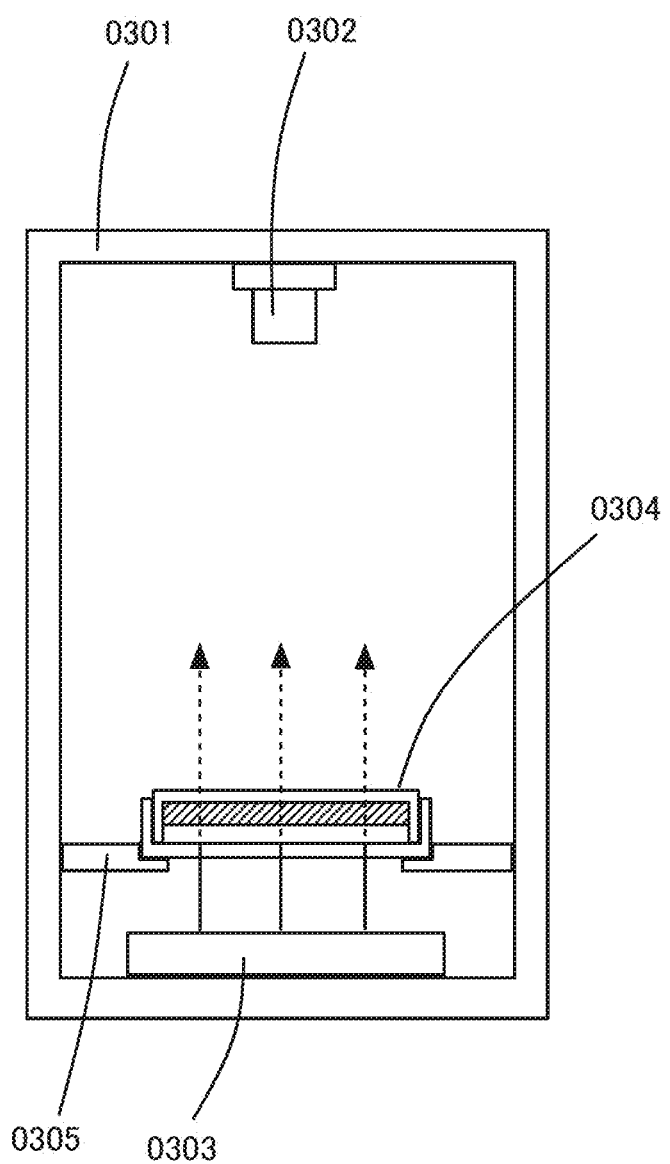
FIG. 3 is a schematic diagram showing an aspect of placing an observation subject in a posture with a petri dish lid set to a lower side.

Moreover, the petri dish may be placed in a posture in which the posture shown in FIG. 1 is vertically reversed. FIG. 3 is a schematic diagram showing an aspect of placing the observation subject in such a case. Illustration outside the dark-environment culturing chamber is omitted considering an intention of illustration. As shown in the figure, an "infrared light camera" (0302) is installed in the ceiling portion of a "dark-environment culturing chamber" (0301)

in being directed downward, and an "infrared light source" (0303) is installed on the floor portion in being directed upward in irradiation light. Then, a "petri dish" (0304) serving as the observation subject is placed in an "observation-subject holding unit" (0305) in such a manner that the lid is positioned below.

When the culture is performed using a solid medium such as the agar medium, the petri dish is left to stand in the posture in which the lid is positioned above until a melted agar medium is solidified in both the pour plate method or the spread plate method. Then, the petri dish is turned upside down into the posture in which the lid is positioned downward after the agar medium is solidified and is kept in the culturing chamber, which is generally performed. When the culture is performed in the posture in which the lid is positioned above, a moisture content evaporated from the medium is condensed on a surface of the lid into water drops, and the water drops fall down on the medium surface in several cases. Such occurrence causes a change in culture conditions on the medium surface, disturbance on photographing of the medium, or the like to hinder the operation in properly performing colony counting. Therefore, the petri dish is placed in such a manner that the lid is positioned below, as described above.

In the dark-environment simultaneous culturing-observing apparatus of the present embodiment, the colonies are observed by photographing the observation subject while the culture is performed. Accordingly, a configuration is preferably formed in such a manner that the petri dish is placed in the posture preferable for culturing the observation subject and the observation subject can be suitably photographed with keeping the posture. When the observation subject is prepared by pouring the subject thereinto, as described above, the petri dish is preferably placed in such a manner that the lid is positioned below, and simultaneously the infrared light camera is preferably installed so that a bottom of the petri dish can be photographed.

Figure 4:
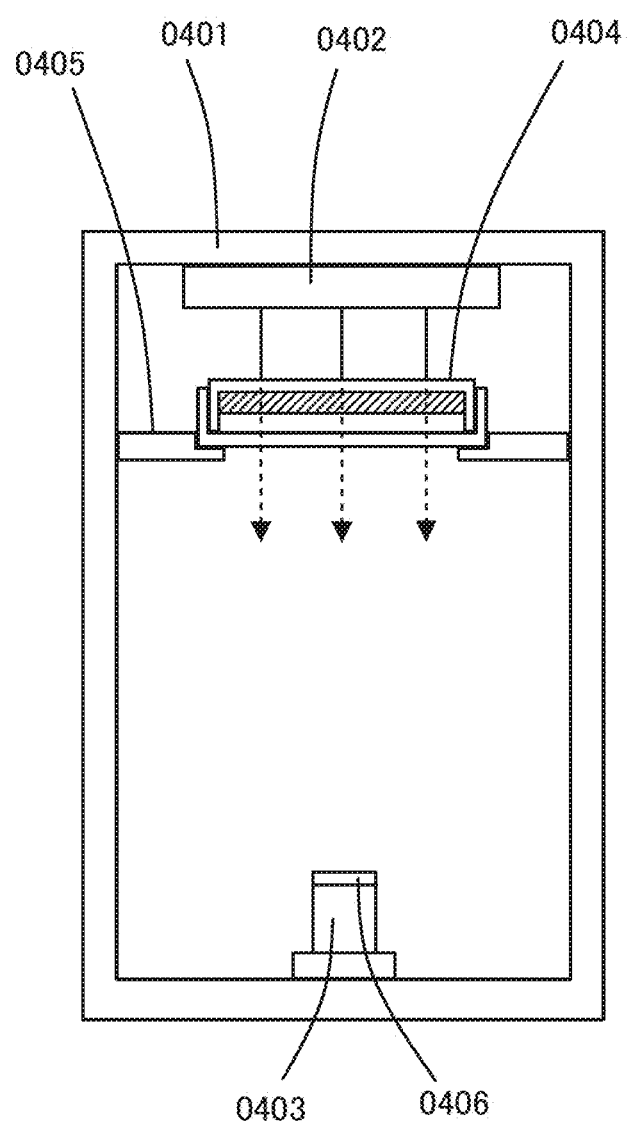
FIG. 4 is a schematic diagram showing a positional relationship in each configuration when an observation subject is a sample applied onto a medium surface.

Moreover, when the sample is applied onto the surface of the medium and cultured, the posture of the petri dish preferable for the culture is in the posture in which the lid is positioned below for the above-described reason. In order to photograph the medium surface on which the sample is spread in this posture, it is necessary to install the infrared light camera on a side of the lid of the petri dish. FIG. 4 is a schematic diagram showing a positional relationship in each configuration when the observation subject is the petri dish in which the medium according to the spread plate method is kept. As shown in the figure, an "infrared light source" (0402) is installed in a ceiling portion of a "dark-environment culturing chamber" (0401) in being directed downward so that the subject may be irradiated with infrared light, and an "infrared light camera" (0403) is installed on a floor portion in being directed upward. Then, a "petri dish" (0404) is placed on a "jig" (0405) in such a manner that the lid is positioned below.

When components are thus arranged in each configuration, a configuration is preferably formed, in which a "cover" (0406) or the like covering the lens of the infrared light camera in a freely openable and closable manner is provided, and the cover is opened only upon photographing the subject. If the lens is directed upward and remains naked, the dust or the like existing in the dark-environment culturing chamber falls down on the lens surface and adheres thereto in several cases. The dust or the like adhered thereto becomes a noise of the photographed image to hinder proper photographing, and therefore a lens cover covering the lens is preferably provided in order to prevent such occurrence.

Figure 5:
FIG. 5(a) shows an image obtained by photographing an observation subject in the present embodiment.
FIG. 5(b) shows an image obtained by photographing an image with visible light by using a general camera.
Figure 5:
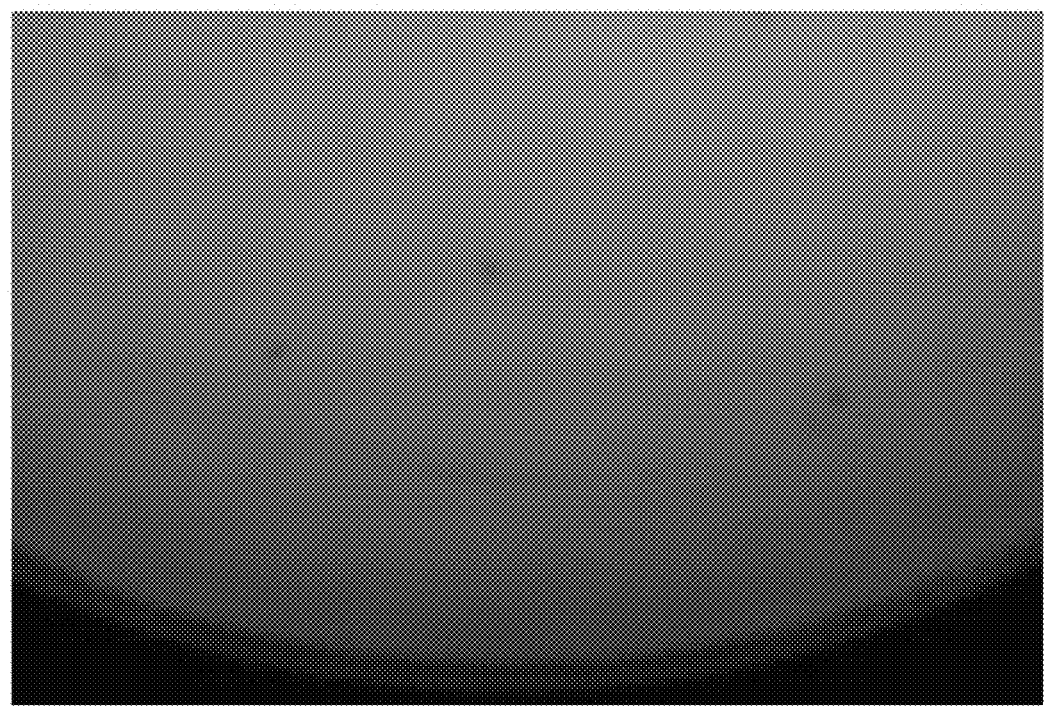

An example of the image of the medium photographed with the dark-environment simultaneous culturing-observing apparatus of the present embodiment configured as described above is shown in FIG. 5 along with an image according to a conventional technology. FIG. 5 shows a photographed image (a) of the observation subject in the present embodiment, and an image (b) obtained by photographing an image with visible light by using a general camera.

Figure 6:
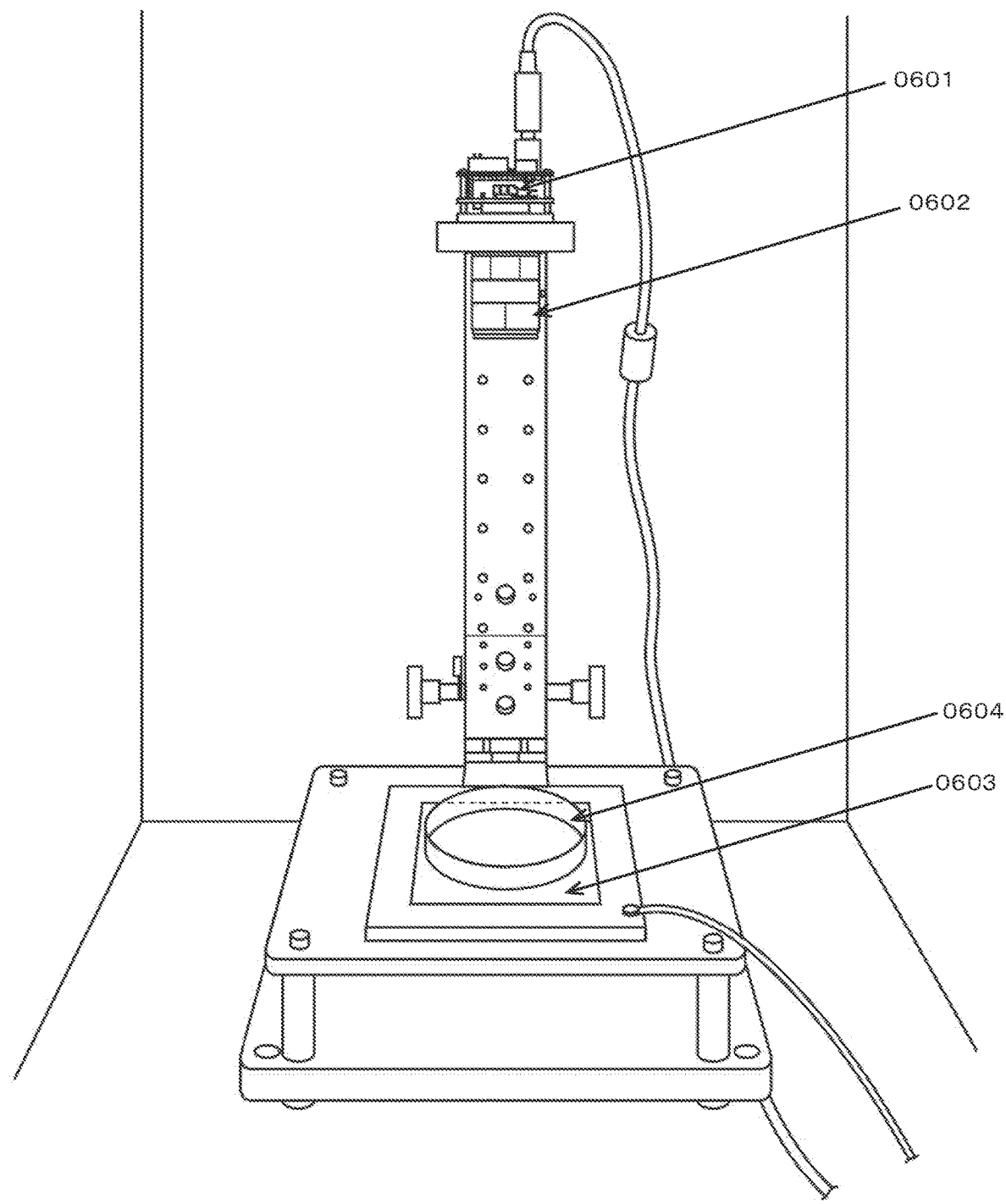
FIG. 6 is a diagram showing a photograph of an apparatus with which the image in FIG. 5(a) is photographed.

FIG. 6 shows a photograph of an apparatus with which the image in FIG. 5(a) is photographed. The image is photographed by wholly covering the apparatus shown therein so as to prevent entry of visible light. In the apparatus, "ART-CAM-1000 MI-WOM-OP (Artray Co., Ltd.)" is used as an "infrared light camera" (0601), and "TS VIS-NIR compact fixed focus lens 16 MM (Edmund Optics Japan, Inc.) " is used as a lens. Moreover, as a "filter" (0602) for cutting off a wavelength shorter than 875 nm, being in a near-infrared wavelength region, "0D4 long-pass filter 875 NM (Edmund Optics Japan, Inc.)" is used. Moreover, as an LED serving as a light-emitting element of an "infrared light source" (0603), "SHF-487-880NM (OSRAM Opto Semiconductors GmbH)" is used. Then, as an "observation subject" (0604), an agar medium prepared by pouring cow's milk thereinto is used, on assumption of inspection of viable bacteria counts.

On the other hand, FIG. 5(b) shows an image of the same medium in FIG. 5(a) obtained by photographing the medium by using a 10 million-pixel camera with the same resolution as the resolution of the above-described infrared light camera, using a filter for cutting off a wavelength longer than 650 nm, and using a white LED as the light source.

As shown in the figure, contrast between bacteria shade and the medium in the image in FIG. 5(a) is clear and a contour of the bacteria shade is also clearly photographed. On the other hand, in the image in FIG. 5(b), the bacteria shade is weak, the contrast is ambiguous and the contour of the bacteria shade is not clearly photographed, either. Accordingly, in the image in FIG. 5(b), the detection is unable to be made unless shade and shadow are further increased by waiting for further growth of bacteria, resulting in delayed detection.

As is known from the above-described results, even in the case of applying, as the subject, the depthwise distribution bacteria source medium being the medium prepared according to the pour plate method in which colony detection is more difficult in comparison with the case of the spread plate method, it is found that the shade showing existence or nonexistence of the colonies is clearly photographed. Accordingly, the dark-environment simultaneous culturing-observing apparatus of the present embodiment can be referred to be preferable for detecting, with high definition, a colony detection subject particularly according to the pour plate method or the membrane filter method by photographing the subject by irradiating the subject with infrared light with high transmissivity and difficulty in scattering.

Embodiment 1 Effect

According to the dark-environment simultaneous culturing-observing apparatus of the present embodiment, the culture and photographing of the observation subject can be performed within one apparatus, and simultaneously the image having excellent resolution can be photographed with infrared light, and colony counting can be performed at early timing.

Embodiment 2

Embodiment 2 Outline

The present embodiment has features of having a control unit for controlling an aspect of photographing an observation subject with an infrared light camera in the dark-environment simultaneous culturing-observing apparatus in Embodiment 1. Thus, the observation subject can be photographed in various aspects.

Figure 7:
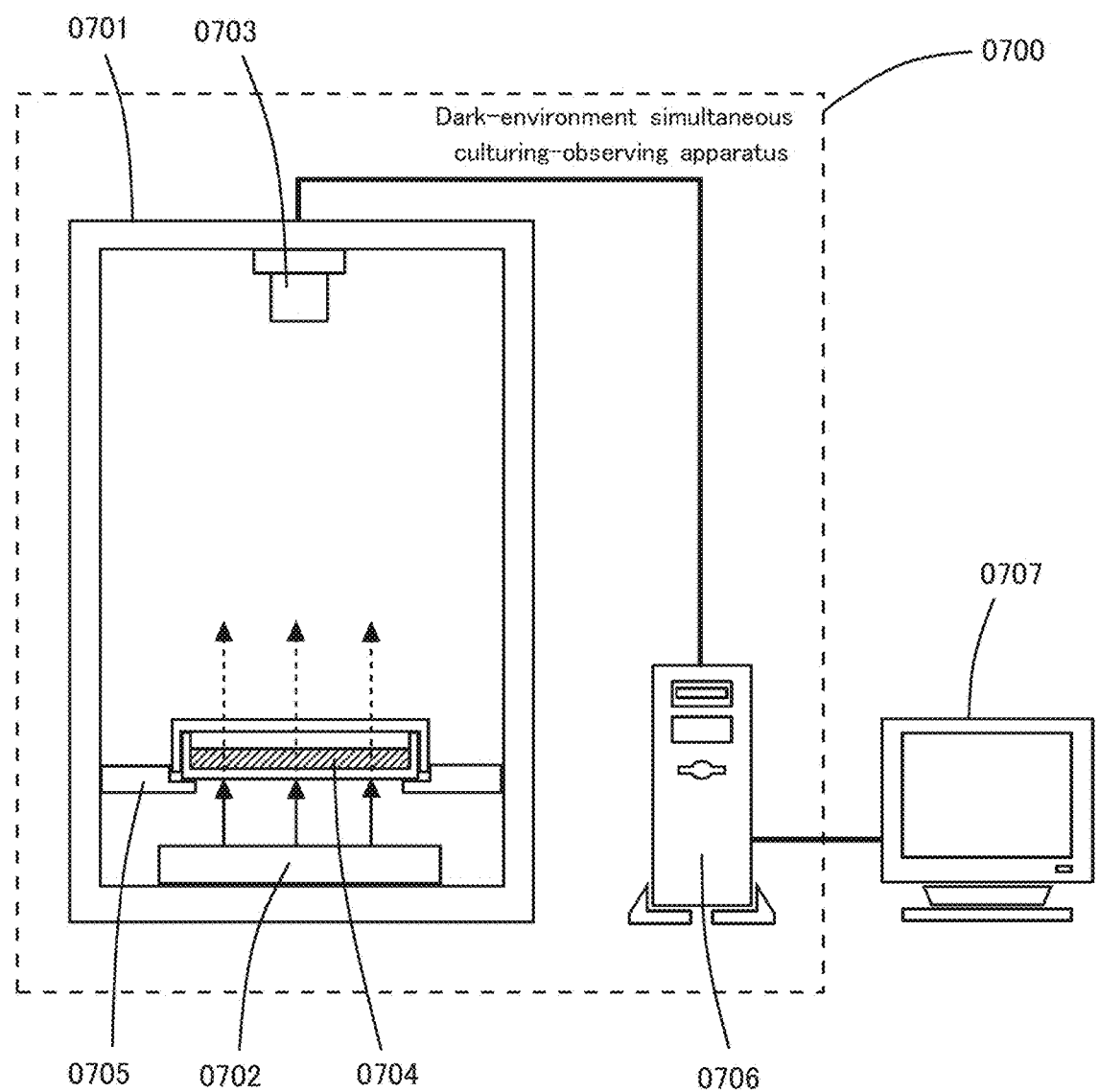
FIG. 7 is a schematic diagram showing each configuration of a dark-environment simultaneous culturing-observing apparatus in Embodiment 2.

FIG. 7 is a schematic diagram showing each configuration of a dark-environment simultaneous culturing-observing apparatus of the present embodiment. As shown in the figure, a "dark-environment simultaneous culturing-observing apparatus" (0700) has a "dark-environment culturing chamber" (0701), an "infrared light source" (0702), an "infrared light camera" (0703), an "observation-subject holding unit" (0705) for holding an "observation subject" (0704), and a "control unit" (0706). As one example of embodying the control unit in the present figure, a "computer" is shown. Moreover, a "display" (0707) for outputting a photographed image, the results of colony counting or the like may be connected to the computer. Each configuration other than the control unit is similar to each configuration in Embodiment 1, and therefore the description herein is omitted.

The "control unit" (0706) fulfills a function of performing multiple photographing control for continuously photographing the observation subject with the infrared light camera and/or for performing moving image control for continuously photographing moving images of the observation subject over multiple times.

In a specific aspect of the multiple photographing control, for example, photographing is controlled in such a manner that a first-time still image is photographed upon culture start, and then the still images are continuously photographed over 48 hours at an interval of 30 minutes. Moreover, photographing may be controlled in such a manner that a photographing interval in a stage of commencement of culture is set to a relatively long period of time, and the photographing interval in a stage in and after the commencement is set to a relatively short period of time. For example, photographing is controlled in such a manner that the period from culture start to six hours is taken as the commencement, and the photographing interval during the period is set to 120 minutes, and for the period after elapse of six hours from the culture start, the photographing interval is set to 30 minutes. The reason therefor is that a reasonable period of time is taken until the bacteria start division, and simultaneously once the division starts, redivision sequentially occurs.

Moreover, when the observation subject is a container in which the medium according to a pour plate method is stored, photographing may be controlled while a focus of the infrared light camera is changed. For example, when a depth of the medium stored in the container is 5 mm, the focus is put on the medium surface to perform photographing, and then while the focus is further changed by 1 mm depthwise in the medium, photographing is performed each time to acquire 5 images in total. The colonies scattered also depthwise in the medium can be detected by performing colony counting on each image thus acquired. Moreover, in place of photographing the observation subject while shifting the focus, photographing may be performed each time while a distance between the observation subject and the infrared light camera is changed by configuring a position of the observation-subject holding unit to be freely variable.

Moreover, the control unit may also be configured so as to simultaneously perform control of infrared light irradiation from the infrared light source, which is indispensable for photographing the subject with the infrared light camera. For example, the control unit may be configured to control the infrared light source so as to irradiate the observation subject with infrared light on a timely basis, for example, when the irradiation is required for photographing the observation subject with the infrared light camera.

The control unit is configured of either hardware or software, or both of the hardware and the software, for example. Specific one example for realizing the hardware and the software includes, when a computer is utilized, hardware configured of a CPU, a bus, a memory, an interface, a peripheral device and the like, and software executable on the hardware. A function of each unit is realized by data on the memory or processing, saving, outputting or the like of the data input through the interface by sequentially executing, as the software, programs developed on the memory.

Figure 8:
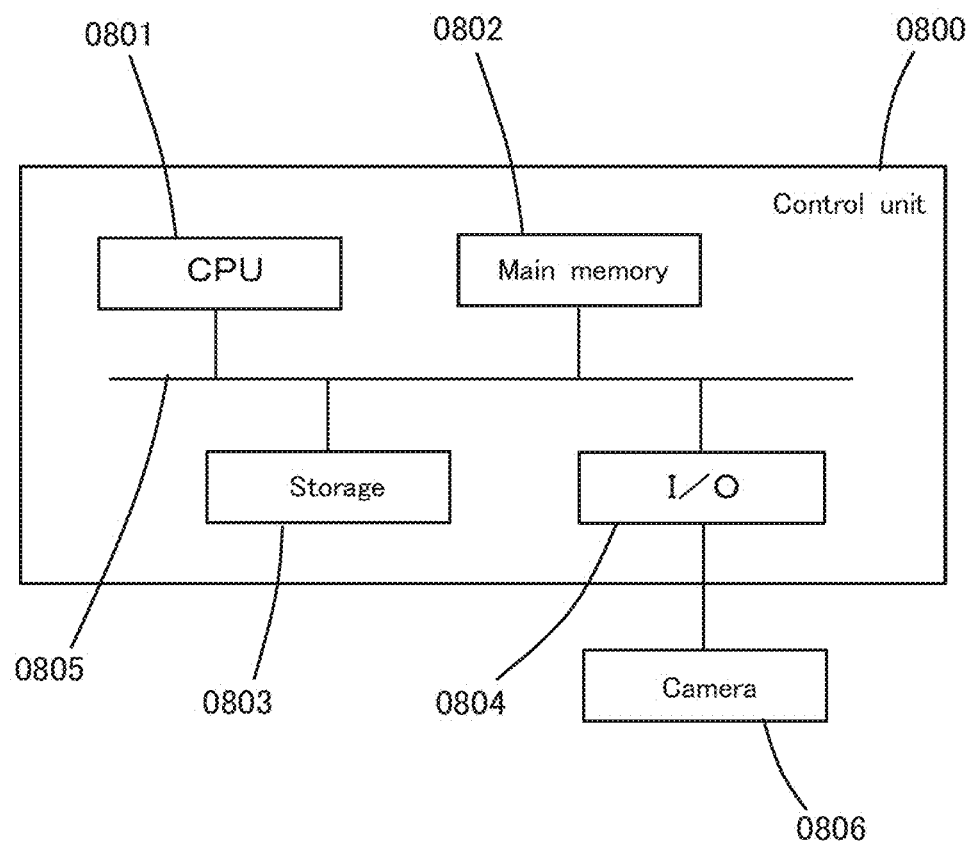
FIG. 8 is a schematic diagram showing one example of a hardware configuration of a control unit.

FIG. 8 is a diagram showing a specific hardware configuration of the control unit. As shown in the figure, a "control unit" (0800) has a "CPU" (0801) for executing various levels of arithmetic processing, a "main memory" (0802) for reading a program for executing various levels of arithmetic processing to allow the CPU to execute the program, and simultaneously providing a work region of the program, a "storage" (0803) for storing a program for controlling an infrared light camera or information such as a photographing interval and a photographing schedule, being control conditions, and an "I/O" (0804) for transmitting and receiving a signal to and from an "infrared light camera" (0806) and the like, in which the units are interconnected mutually through a data communication pathway such as a system bus (0805) to transmitting and receiving the information or processing the information. In addition, when irradiation from the infrared light source is controlled with the control unit, the signal is transmitted and received through I/O in a manner same as in the infrared light camera.

Processing in the control unit is shown by taking a case where multiple photographing control is performed as an example. For example, with the CPU, the program for multiple photographing control stored in the storage is first developed in the work region of the main memory to execute the program to read an image pickup interval to be stored in the storage, and then to apply, to the infrared light camera, processing for outputting the signal for allowing the infrared light camera to pick up the image through I/O according to the read value.

Moreover, when control of irradiation of the infrared light source is performed with the control unit, with the CPU, the program for controlling the infrared light source as stored in the storage is developed in the work region of the main memory to execute the program to read the irradiation interval and irradiation time stored in the storage, and then to apply processing for outputting the signal for allowing the infrared light source to pick up the image to the infrared light source through I/O according to the read value.

Figure 9:
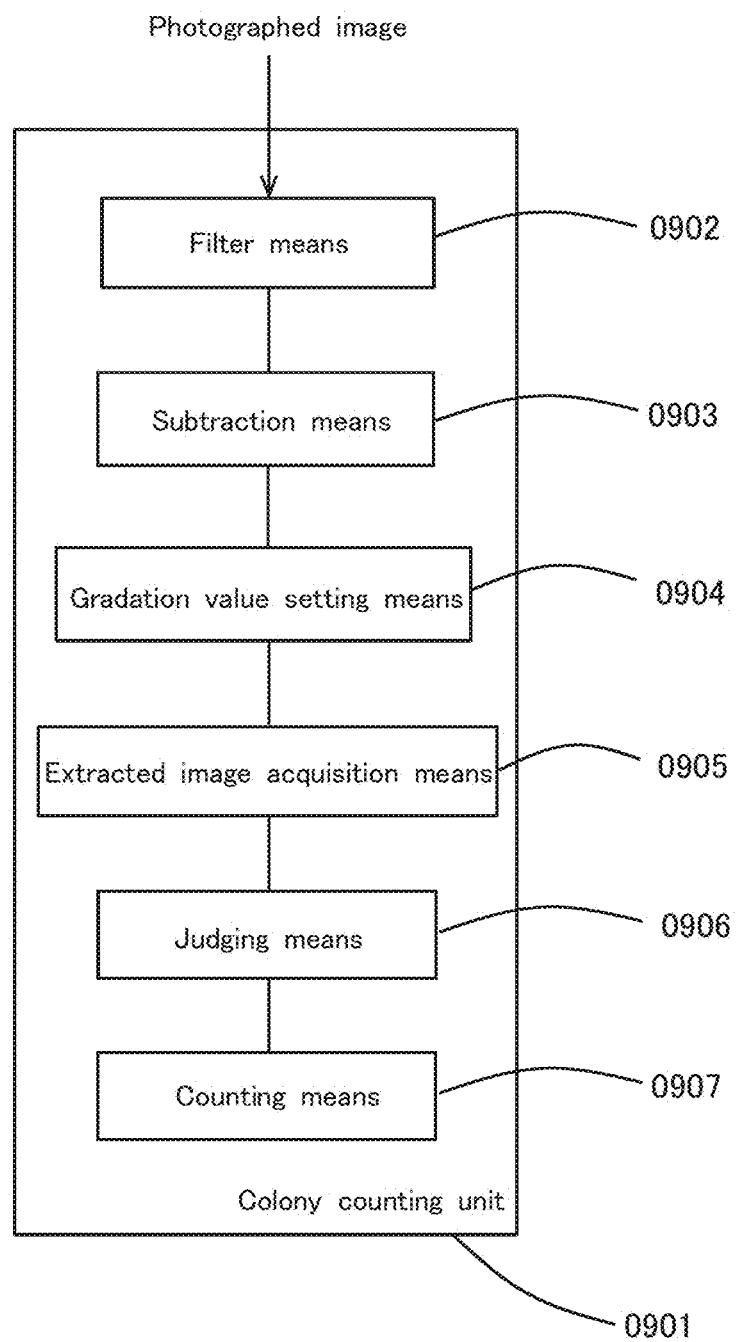
FIG. 9 is a functional block diagram showing one example of a colony detection unit.

Moreover, the dark-environment simultaneous culturing-observing apparatus of the present embodiment may have a colony counting unit for performing colony counting based on the image photographed with the infrared light camera. FIG. 9 is a schematic diagram showing one example of a colony detection unit. As shown in the figure, a "colony detection unit" (0901) has a "filter means" (0902), a "subtraction means" (0903), a "gradation value setting means" (0904), an "extracted image acquisition means" (0905), a "judging means" (0906) and a "counting means" (0907). The colony counting unit can be realized by the above-described hardware configuration and the like.

With the "filter means" (0902), a digital image photographed with the infrared light camera is converted into a gray scale, and partial shade, such as turbidity of the medium is eliminated by applying a low pass filter thereto. With the "subtraction means" (0903), the image from which the partial shade is eliminated with the filter means is subtracted from the above-described gray scale image to obtain an image from which an offset value is subtracted.

With the "gradation value setting means" (0904), multiple gradation values are set with a prescribed interval between a maximum gradation value and a minimum gradation value of the image obtained with the subtraction means. With the "extracted image acquisition means" (0905), only pixels darker than each gradation value set up with the gray scale value setting means are extracted from the image obtained with the subtraction means to obtain multiple binarized extracted images corresponding to respective gradation values.

With the "judging means" (0906), a region other than a circular region darker than the gradation value corresponding thereto is removed from each extracted image obtained with the extracted image acquisition means to judge, as the colonies, a region that is dark in a central portion and becomes stepwise lighter toward a circumference thereof. With the "counting means" (0907), the colonies judged are counted. Colony counting may be performed, for example, every time when the observation subject is photographed, or at timing different from photographing timing.

Moreover, the "colony detection unit" (0901) may further have a means for performing various levels of processing based on the counting results with the counting means. For example, the "colony detection unit" (0901) may have a means for applying, as a threshold, a predetermined counting value preset to output an alarm with a sound, an image or the like when the counting results with the counting means are over the threshold. Alternatively, the "colony detection unit" (0901) may have a means for visually displaying, with a graph or the like, transition of the counting results with elapse of time from culture start.

Moreover, the "colony detection unit" (0901) may have a means for accumulating various pieces of information on colony counting, for example, information on a sample, a medium, culture conditions, counting results, and transition of the counting results, to create a database. Then, the "colony detection unit" (0901) may also have a means for applying processing thereto with reference to the database. For example, the "colony detection unit" (0901) may have a means for comparing transition of the counting results, while the transition of the counting results is actually recorded, with transition of the counting results of the same observation subject accumulated in the database to compute a difference therebetween. Alternatively, the "colony detection unit" (0901) may have a means for computing a difference from a control being only a medium containing no sample. Then, the "colony detection unit" (0901) may have a means for outputting some kind of alarm when the computed difference described above is over a predetermined threshold.

Moreover, the "colony detection unit" (0901) may have a means for estimating colony counts after elapse of 24 hours or 48 hours from culture start on the sample provided with a bacteria source contained in the observation subject with reference to the information accumulated in the database. When the colony counts after elapse of 24 hours or 48 hours estimated by the above-described means are in a permissible value or less, safety standards of food or the like from which the sample is provided are regarded to be satisfied, and the food or the like is immediately put in a distribution route and shipped to a distributor or the like. Then, the colony counts counted in an actual observation subject after elapse of 48 hours from culture start are confirmed to be in the permissible value or less, and then the shipped food or the like is put on the market. The food or the like can be further quickly put on the market by estimating the colony counts as described above, in comparison with a case where colony counting is actually performed after elapse of 48 hours, safety is confirmed, and then the food or the like in put in the distribution route. More specifically, the present art can produce benefits of capability of providing the market with the food or the like with higher freshness.

Moreover, the "colony detection unit" (0901) may have a means for computing an expiration date or a best-before date on the sample provided with the bacteria source contained in the observation subject with reference to the information accumulated in the database. For example, a time to exceeding permissible bacterial counts in consumption of raw meat is computed based on the information accumulated in the database. Then, the expiration date of the raw meat serving as the sample is computed from the computed time and a time from which the culture is started.

Embodiment 2 Effect

According to the dark-environment simultaneous culturing-observing apparatus of the present embodiment, suitable photographing of the observation subject can be performed according to the observation subject, the culturing method or the like.

Embodiment 3

Embodiment 3 Outline

The present embodiment shows a dark-environment simultaneous culturing-observing apparatus in which Embodiment 1 or Embodiment 2 is applied as a base, and infrared light cameras and observation subjects are in a many-to-many relationship.

Embodiment 3 Configuration

A case where the infrared light camera and the observation subject is in a one-to-one relationship has been described so far. However, the dark-environment simultaneous culturing-observing apparatus of the present embodiment can also be applied to a case where the infrared light cameras and the observation subjects are in a many-to-many relationship. For example, a configuration may be formed in such a manner that a rack capable of housing, in a multi-stage manner, trays on which multiple petri dishes are placed is provided in a dark environment culturing chamber, and infrared light cameras in the number same with the number of the petri dishes to be place on one tray are attached onto a robot arm, and the infrared light cameras are conveyed to each tray by the robot arm to photograph the observation subjects. Moreover, a configuration can also be formed in such a manner that infrared light cameras and an infrared light source are fixed, and trays on which petri dishes are placed are sequentially conveyed to a photographing place to photograph the observation subjects.

Figure 10:
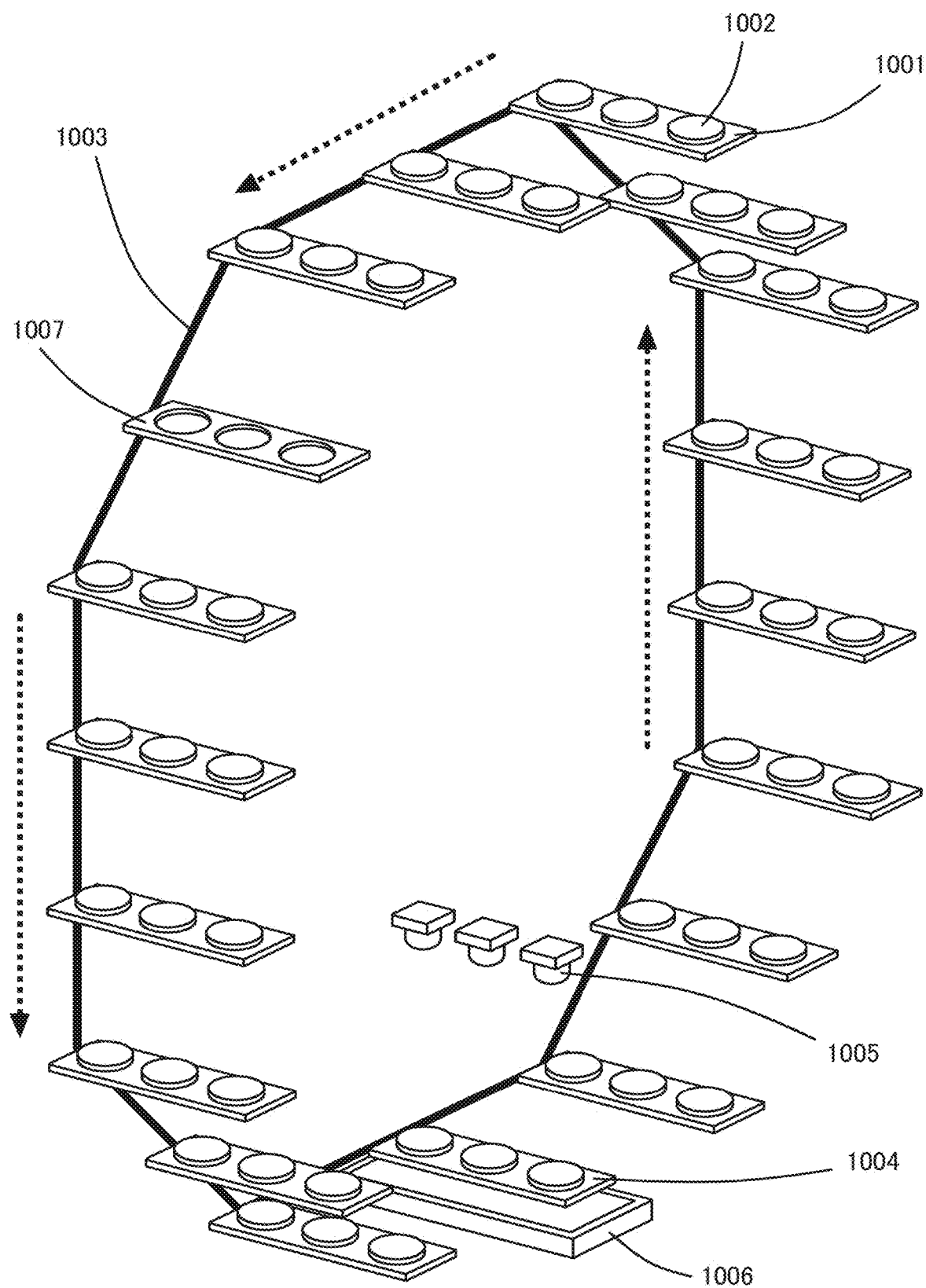
FIG. 10 is a schematic diagram showing a case formed into a configuration in which observation subjects are photographed while trays are sequentially conveyed.

FIG. 10 is a schematic diagram showing a case of forming a configuration in which observation subjects are photographed while trays are sequentially conveyed. In addition, in the present figure, an aspect in a dark-environment culturing chamber is conceptualized, in which infrared light cameras, an infrared light source and observation subjects are mainly shown.

As shown in the figure, three "petri dishes" (1002) serving as the observation subjects are placed on one "tray" (1001). Then, a configuration is formed in such a manner that eighteen petri dishes in total are circulated in directions shown by dotted line arrows along an annular "guide rail" (1003) shown by a thick line in the figure, while a predetermined posture is maintained. Such a configuration is realized in cooperation with power such as a motor, a transmission means for transmitting the power to each plate along the guide rail, such as a belt and a chain, a power control means configured of a computer in order to control the power, and the like. Moreover, a configuration may be formed, in which multiple trays are attached onto a rotary drum in a predetermined posture, in place of the guide rail, and conveyed by rotation of the drum.

As described later, controlling of photographing the subject with the infrared light camera and control for conveying the trays to be photographed to a predetermined photographing place are closely related. Therefore, a configuration may be formed, in which tray conveyance is also controlled with the control unit.

Then, an "infrared light camera" (1005) for photographing one of all the petri dishes placed on a "tray" (1004) conveyed to a lower end of the guide rail and an "infrared light source" (1006) is installed in a position preferable for photographing the observation subject. In addition, in a "tray" (1007) in a state of no petri dish being placed thereon, places on which the petri dishes are planned to be placed are open.

Here, when the photographing interval of the observation subject is set to 45 minutes with the control unit, power only needs to be controlled in such a manner that one tray is conveyed to the photographing place every 45 minutes. Specifically, the power only needs to be controlled with the power control means in such a manner that respective trays are sequentially conveyed to the photographing place at an interval of 2.5 minutes. Then, with the control unit, only the infrared light camera only needs to be controlled in such a manner that the tray conveyed at the interval of 2.5 minutes according to control with the power control means is photographed.

Embodiment 3 Effect

According to the dark-environment simultaneous culturing-observing apparatus of the present embodiment, the culture and observation of multiple observation subjects can be efficiently performed, and labor saving in colony counting can be much further achieved.

Embodiment 4

Embodiment 4 Outline

The present embodiment relates to a culturing-observing method using any one of the dark-environment simultaneous culture apparatuses in Embodiments 1 to 3.

Embodiment 4 Configuration

Figure 11:
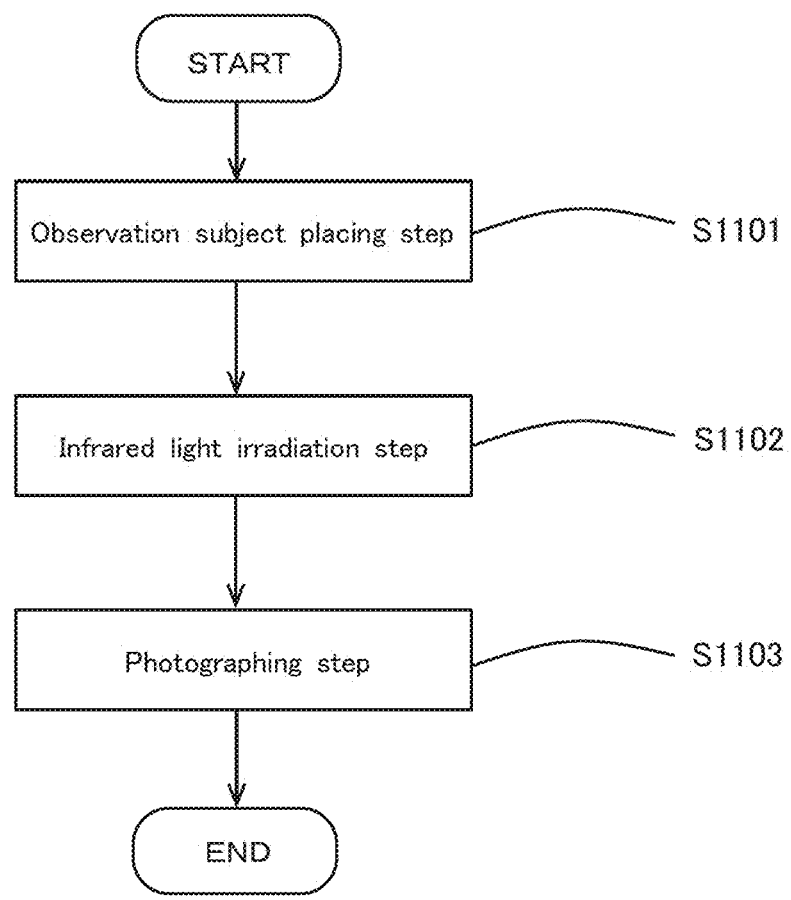
FIG. 11 is a flow diagram showing one example of a culturing-observing method in Embodiment 4.
Figure 12:
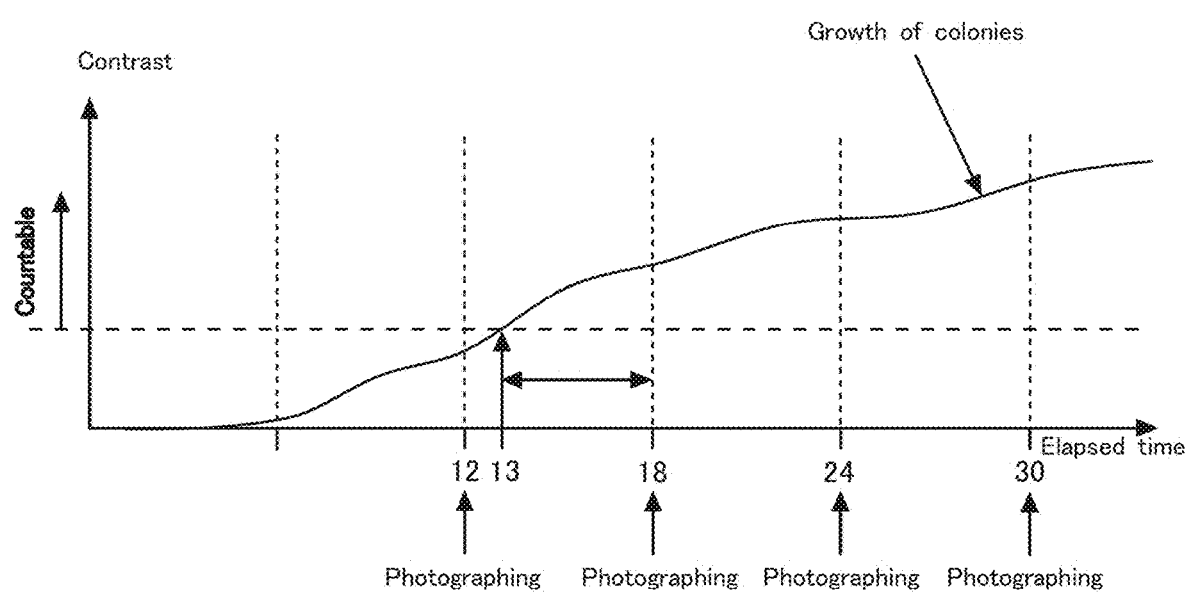
FIG. 12 shows growth of colonies and countable contrast with time elapse.

FIG. 11 is a flow diagram showing one example of a culturing-observing method of the present embodiment. As shown in the figure, the culturing-observing method of the present embodiment has an "observation subject placing step" (S1101), an "infrared light irradiation step" (S1102) and a "photographing step" (S1103).

In the "observation subject placing step" (S1101), an observation subject prepared by adding a bacteria source to a medium is placed in a dark-environment culturing chamber of the dark-environment simultaneous culturing-observing apparatus in order to culture bacteria in a dark environment. For example, when culture is performed according to a spread plate method, a sample is spread onto a surface of a medium prepared by pouring a melted agar medium or the like into a petri dish or the like and then being solidified, and the bacteria source is added thereonto. Then, the petri dish or the like is placed in the dark-environment culturing chamber.

In the "infrared light irradiation step" (S0902), the observation subject kept in the dark-environment culturing chamber is irradiated with infrared light from the above-described infrared light source. Moreover, the observation subject may be irradiated with infrared light on a timely basis, for example, when irradiation is required for photographing the observation subject with an infrared light camera. In order to irradiate the subject on the timely basis, for example, the subject is irradiated therewith by executing a program for infrared light source control as stored in the storage with a CPU, based on the hardware configuration or the like shown in Embodiment 2.

In the "photographing step" (S0903), the observation subject is photographed with the infrared light camera in a state in which the observation subject is irradiated with infrared light from the infrared light source. Moreover, when the dark-environment simultaneous culturing-observing apparatus in Embodiment 2 or 3 is used, the photographing step may further have a control substep for performing multiple photographing control for continuously photographing the observation subject with the infrared light camera and/or for performing moving image photographing control for continuously performing photographing of moving images of the observation subject over multiple times. When multiple photographing control is performed, for example, first-time photographing is performed upon culture start, and then photographing is continuously performed over 48 hours at an interval of 11 minutes. In order to control photographing in such a manner, for example, control is performed by executing a program for controlling photographing the subject with the infrared light camera as stored in the storage with a CPU, based on the hardware configuration and the like shown in Embodiment 2.

The images photographed through respective steps described above are provided for visual observation, or for execution of an image processing program for colony counting, a colony counting program or the like. In addition, various programs for colony counting or devices for executing, processing or the like thereof can be realized using each configuration in Embodiment 2 or a known technology.

Moreover, the observation subject placing step may have a depthwise distribution bacteria source medium production substep for producing a depthwise distribution bacteria source medium by pouring a bacteria source into a medium raw material. More specifically, when culture is performed by a pour plate method, a melted agar medium or the like and a sample serving as the bacteria source are mixed and then solidified. A container such as a petri dish in which the thus produced depthwise distribution bacteria source medium is stored is placed in the dark-environment culturing chamber.

Embodiment 4 Effect

According to the culturing method of the present embodiment, the culture and photographing of the observation subject can be performed within one apparatus, and simultaneously the image having excellent resolution can be photographed with infrared light, and colony counting can be performed at early timing.

The invention claimed is:

1. A dark-environment simultaneous culturing-observing apparatus comprising:
a dark-environment culturing chamber configured by a closed container, the dark-environment culturing chamber having an entirely dark interior when the dark-environment culturing chamber is in a closed state, the dark-environment culturing chamber being configured to prevent visible light from entering into the dark-environment culturing chamber when the dark-environment culturing chamber is in the closed state;
a plurality of observation-subject holders disposed inside the interior of the dark-environment culturing chamber, the plurality of observation-subject holders being spaced apart from each other;
a rotating mechanism connected to each of the plurality of observation-subject holders to rotate the plurality of observation-subject holders at a predetermined speed in a state in which each of the plurality of observation-subject holders maintains a predetermined posture while rotating, a connection state of the plurality of observation-subject holders being in a generally circular shape;
a plurality of observation subjects held by the plurality of observation-subject holders, respectively, inside the interior of the dark-environment culturing chamber, each of the observation subjects including a culturing bacteria;
an infrared light source disposed inside the interior of the dark-environment culturing chamber at a first side of the observation subject when one of the plurality of observation-subject holders is located at an observation position by the rotating mechanism, the infrared light source being configured to irradiate infrared light through the observation subject while the interior is entirely dark;
an infrared light camera disposed inside the interior of the dark-environment culturing chamber at a second side of the observation subject opposite to the first side when one of the plurality of observation-subject holders is located at the observation position by the rotating mechanism, the infrared light camera being configured to capture the infrared light that passes through the observation subject located at the observation position while the interior is entirely dark and to create an image of the observation subject based on the captured infrared light;
a memory configured to store a program; and
a processor configured to execute the program so as to:
convert the created image into a converted image in gray scale;
identify each pixel among pixels forming the converted image that is darker than a predetermined value as an identified pixel;
identify a colony of the culturing bacteria based on a shape of each identified pixel; and
count a number of the identified colonies of the culturing bacteria,
wherein, when a predetermined period of time passes, a plurality of the images of the plurality of observation subjects on the plurality of observation-subject holders are created, and
the processor is configured to perform the conversion of each of the plurality of the created images, the identification of the each pixel, the identification of each of the colonies, and the counting of the number of the identified colonies.

2. The dark-environment simultaneous culturing-observing apparatus according to claim 1,
wherein the processor is configured to cause the infrared light camera to capture the infrared light that has passed through the observation subject multiple times and to create a plurality of the images of the same observation subject when one of the plurality of observation-subject holders is located at the observation position by the rotating mechanism, and
the processor is configured to detect the number of the identified colonies of the culturing bacteria from each of the plurality of the created images of the same observation subject.

3. The dark-environment simultaneous culturing-observing apparatus according to claim 1,
wherein the infrared light is a near-infrared light.

4. The dark-environment simultaneous culturing-observing apparatus according to claim 1,
wherein the infrared light source is provided with a filter configured to block a predetermined wavelength band of the infrared light that is irradiated from the infrared light source.

5. The dark-environment simultaneous culturing-observing apparatus according to claim 1,
wherein the infrared light camera is provided with a filter configured to block a predetermined wavelength band of the infrared light that has passed through the observation subject.

6. The dark-environment simultaneous culturing-observing apparatus according to claim 1,
wherein each of the plurality of observation subjects is a depthwise distribution bacteria source medium formed by pouring a bacteria source into a medium,
the processor is configured to cause the infrared camera to create a plurality of the images of the observation subject that are focused on different depths of the depthwise distribution bacteria source medium when one of the plurality of observation-subject holders is located at the observation position by the rotating mechanism, and
the processor is configured to detect the number of the identified colonies of the culturing bacteria from each of the plurality of the created images of the same observation subject.

7. The dark-environment simultaneous culturing-observing apparatus according to claim 1, wherein
the infrared light camera is directed downward on in the dark-environment culturing chamber;
the infrared light source is directed upward on a floor of the dark-environment culturing chamber; and
one of the observation-subject holders is arranged along an optical axis between the infrared light camera and the infrared light source when one of the plurality of observation-subject holders is located at the observation position by the rotating mechanism.

8. The dark-environment simultaneous culturing-observing apparatus according to claim 7,
wherein each of the plurality of observation subjects is arranged in a membrane filter including the culturing bacteria.

9. The dark-environment simultaneous culturing-observing apparatus according to claim 1,
wherein a wavelength of the infrared light that is captured by the infrared camera is in a range of 0.7 μm to 1000 μm.

10. The dark-environment simultaneous culturing-observing apparatus according to claim 9,
wherein the wavelength of the infrared light that is captured by the infrared camera is in a range of 0.7 μm to 1.0 μm.

11. A culturing-observing method for causing a processor to execute a program stored in a memory, the method comprising executing on the processor the steps of:
preparing a dark-environment culturing chamber that is configured by a closed container, the dark-environment culturing chamber having an entirely dark interior when the dark-environment culturing chamber is in a closed state, the dark-environment culturing chamber being configured to prevent visible light from entering into the dark-environment culturing chamber when the dark-environment culturing chamber is in the closed state;
placing a plurality of observation subjects on a plurality of observation-subject holders, respectively, each of the plurality of observation subjects being obtained by adding a bacteria source to a medium, the plurality of observation-subject holders being spaced apart from each other inside the interior of the dark-environment culturing chamber, each of the plurality of observation-subject holders being connected to a rotating mechanism, a connection state of the plurality of observation-subject holders being in a generally circular shape;
rotating, by the rotating mechanism, the plurality of observation-subject holders that hold the plurality of observation subjects inside the interior of the dark-environment culturing chamber at a predetermined speed in a state in which each of the plurality of observation-subject holders maintains a predetermined posture while rotating;
culturing a bacteria of each of the plurality of observation subjects while the interior is entirely dark;
irradiating infrared light toward a first side of the observation subject kept in the dark-environment culturing chamber while the interior is entirely dark so that the infrared light passes through the observation subject when one of the plurality of observation-subject holders is located at an observation position by the rotating mechanism;
receiving the infrared light that has passed through the observation subject while the interior is entirely dark so as to create an image of the observation subject, when one of the plurality of observation-subject holders is located at the observation position by the rotating mechanism;
converting the created image into a converted image in gray scale;
identifying each pixel among pixels forming the converted image that is darker than a predetermined value as an identified pixel;
identifying a colony of the culturing bacteria based on a shape of each identified pixel; and
counting a number of the identified colonies of the culturing bacteria,
wherein, when a predetermined period of time passes, a plurality of the images of the plurality of observation subjects on the plurality of observation-subject holders are created, and
the processor is configured to perform the conversion of each of the plurality of the created images, the identification of the each pixel, the identification of each of the colonies, and the counting of the number of the identified colonies.

12. The culturing-observing method according to claim 11,
wherein the infrared light that has passed through the observation subject multiple times is received so as to create a plurality of the images of the same observation subject when one of the plurality of observation-subject holders is located at the observation position by the rotating mechanism, and
the number of the identified colonies of the culturing bacteria from each of the plurality of the created images of the same observation subject is detected.

13. The culturing-observing method according to claim 11,
wherein each of the plurality of observation subjects is a depthwise distribution bacteria source medium formed by pouring the bacteria source into the medium,
a plurality of the images of the same observation subject that are focused on different depths of the depthwise distribution bacteria source medium are created when one of the plurality of observation-subject holders is located at the observation position by the rotating mechanism, and
the number of the identified colonies of the culturing bacteria from each of the plurality of the created images of the same observation subject is detected.

14. The culturing-observing method according to claim 11,
wherein a wavelength of the infrared light that is received to create the image of the observation subject is in a range of 0.7 μm to 1000 μm.

15. The culturing-observing method according to claim 14,
wherein the wavelength of the infrared light that is received to create the image of the observation subject is in a range of 0.7 μm to 1.0 μm.

* * * * *